(12) United States Patent
Hwang et al.

(10) Patent No.: US 11,511,463 B2
(45) Date of Patent: Nov. 29, 2022

(54) APPARATUS AND PROCESS FOR CONTINUOUSLY MANUFACTURING MICRONEEDLES

(71) Applicant: LG HOUSEHOLD & HEALTH CARE LTD., Seoul (KR)

(72) Inventors: Young-Min Hwang, Daejeon (KR); Koo-Chul Kwon, Daejeon (KR); Woo-Sun Shim, Daejeon (KR); Nae-Gyu Kang, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 193 days.

(21) Appl. No.: 16/764,312

(22) PCT Filed: Jul. 5, 2018

(86) PCT No.: PCT/KR2018/007655
§ 371 (c)(1),
(2) Date: May 14, 2020

(87) PCT Pub. No.: WO2019/098485
PCT Pub. Date: May 23, 2019

(65) Prior Publication Data
US 2021/0170643 A1 Jun. 10, 2021

(30) Foreign Application Priority Data
Nov. 15, 2017 (KR) .......................... 10-2017-0152488

(51) Int. Cl.
*B29C 41/50* (2006.01)
*A61M 37/00* (2006.01)
(Continued)

(52) U.S. Cl.
CPC ......... *B29C 41/50* (2013.01); *A61M 37/0015* (2013.01); *B29C 41/02* (2013.01);
(Continued)

(58) Field of Classification Search
CPC ....... B29C 41/50; B29C 41/02; B29C 39/026; B29C 39/42; A61M 37/0015;
(Continued)

(56) References Cited

U.S. PATENT DOCUMENTS

2008/0275400 A1* 11/2008 Ferguson ............. B29C 45/561
264/153
2009/0234301 A1 9/2009 Tomono
(Continued)

FOREIGN PATENT DOCUMENTS

CN 102202723 A 9/2011
CN 105643839 A 6/2016
(Continued)

*Primary Examiner* — Cynthia L Schaller
(74) *Attorney, Agent, or Firm* — Birch, Stewart, Kolasch & Birch, LLP

(57) ABSTRACT

The present disclosure relates to an apparatus and a process which can continuously produce microneedles using a conveyor system and decomposition or vacuum. By using the microneedle production method and apparatus according to the present disclosure, continuous mass production of microneedles is available, and therefore it is possible to reduce the input of manpower and produce a large amount of products compared to the conventional production method.

18 Claims, 2 Drawing Sheets

(51) Int. Cl.
  *B29C 41/02* (2006.01)
  *B32B 7/12* (2006.01)
  *B29L 31/00* (2006.01)
(52) U.S. Cl.
  CPC ....... *B32B 7/12* (2013.01); *A61M 2037/0053* (2013.01); *B29L 2031/7544* (2013.01)
(58) Field of Classification Search
  CPC .. A61M 2037/0053; A61M 2037/0046; B32B 7/12; B29L 2031/7544; B29K 2995/0056; B29K 2883/00
  See application file for complete search history.

(56) References Cited

U.S. PATENT DOCUMENTS

| | | |
|---|---|---|
| 2011/0192562 A1 | 8/2011 | Motoi et al. |
| 2012/0193840 A1 | 8/2012 | Kwon |
| 2014/0188041 A1* | 7/2014 | Moore .............. A61M 37/0015 264/309 |
| 2017/0050010 A1* | 2/2017 | McAllister ........ A61M 37/0015 |
| 2017/0217656 A1 | 8/2017 | Yamada |

FOREIGN PATENT DOCUMENTS

| | | |
|---|---|---|
| JP | 2005-198865 A | 7/2005 |
| JP | 4810488 B2 | 11/2011 |
| JP | 2013-162982 A | 8/2013 |
| KR | 10-0846195 B1 | 7/2008 |
| KR | 10-2011-0012986 A | 2/2011 |
| KR | 10-1152486 B1 | 6/2012 |
| KR | 10-2016-0139759 A | 12/2016 |
| KR | 10-2017-0011580 A | 2/2017 |
| KR | 10-2017-0038463 A | 4/2017 |
| KR | 10-2017-0063591 A | 6/2017 |
| WO | WO 2008/062832 A1 | 5/2008 |

* cited by examiner

【FIG. 1】
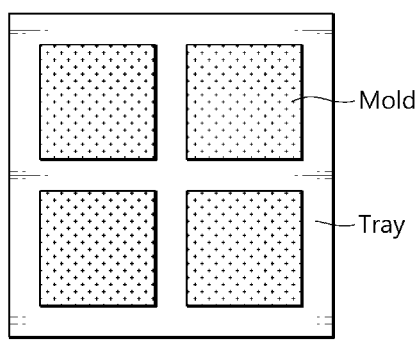
【FIG. 2】
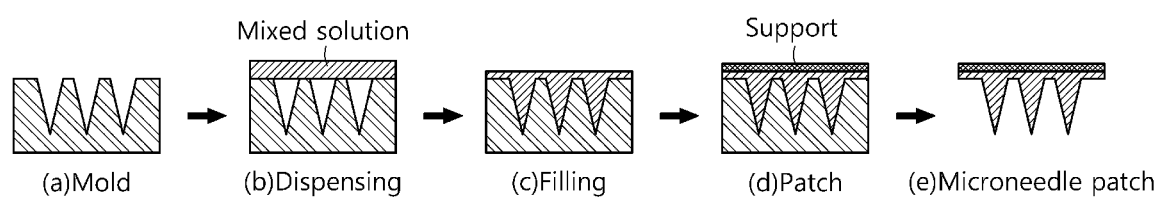

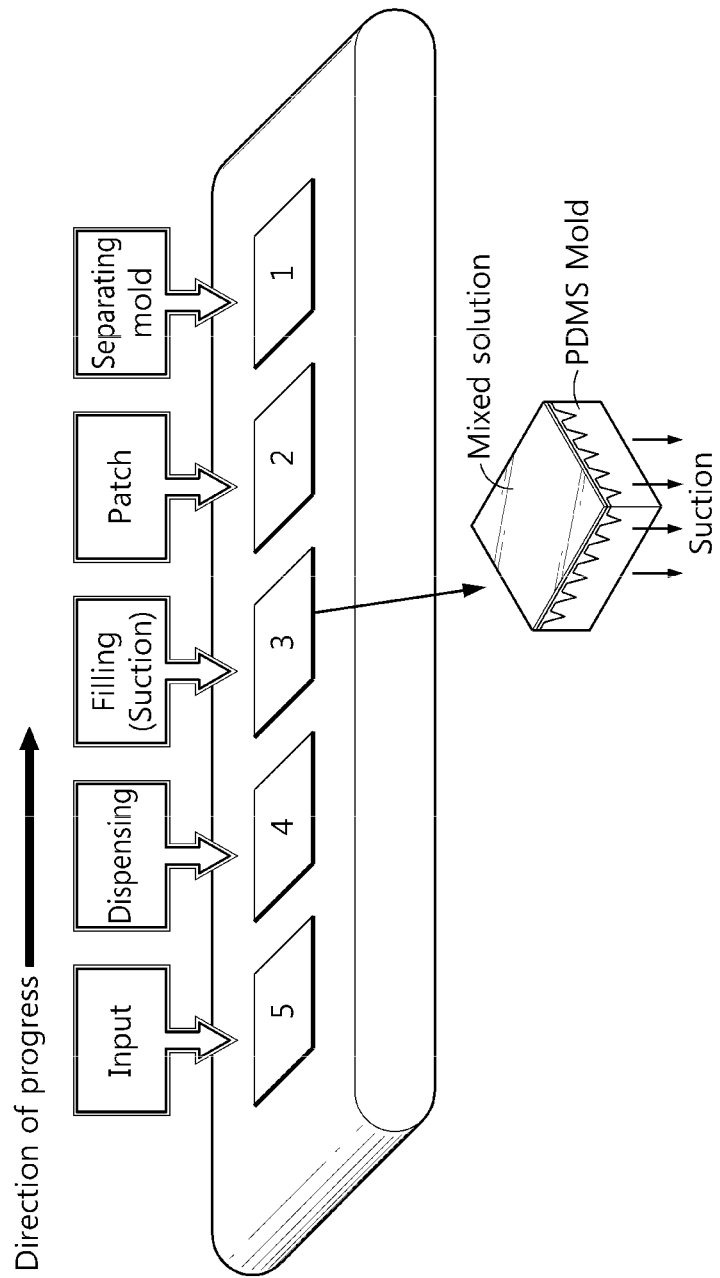

APPARATUS AND PROCESS FOR CONTINUOUSLY MANUFACTURING MICRONEEDLES

CROSS REFERENCE TO RELATED APPLICATIONS

This application is the National Phase of PCT International Application No. PCT/KR2018/007655, filed on Jul. 5, 2018, which claims priority under 35 U.S.C. 119(a) to Patent Application No. 10-2017-0152488, filed in the Republic of Korea on Nov. 15, 2017, all of which are hereby expressly incorporated by reference into the present application.

DISCLOSURE

Technical Field

The present application claims the benefit of priority based on Korean Patent Application No. 10-2017-0152488 filed on Nov. 15, 2017, and the entire contents disclosed in the description and drawings of the corresponding application are incorporated in the present application.

The present disclosure relates to an apparatus and a process for continuous production of microneedles. More specifically, the present disclosure relates to an apparatus and a process which can continuously produce microneedles using a conveyor system and vacuum.

Background Art

Various methods for dermal administration of a target material with high efficiency have been studied. However, since the skin surface layer has a barrier function to prevent foreign substances from entering the body, it is very difficult not only to absorb the target material in an amount sufficient to exert the desired effect, but also to provide the target material to a specific site of the skin surface layer. Moreover, depending on characteristics of the target material, it is particularly difficult to supply a target material with very low bioavailability or pharmacological utilization rate through the skin, such as when skin affinity (lipid affinity) is insufficient or when the molecular weight is too large (500 Daltons or more).

Accordingly, in order to sufficiently supply the target material regardless of the type of the target material to a specific site of the skin surface layer, recently, a microneedle (micropile, micromissile capsule, etc.) technology has been proposed. In general, a microneedle is used for the delivery of an active substance such as a cosmetic active substance, a drug or a vaccine or the like in vivo, detection of an analyte in vivo and biopsy. The delivery of a pharmaceutical or cosmetical active substance using a microneedle is aimed at the delivery of an active substance through skin, rather than a biocirculatory system such as blood vessels or lymphatic vessels.

As a material of the microneedle, a metal or silicon may be used, and may be made of a self-degradable material or a biodegradable material. The method for producing a microneedle composed of a self-degradable material or a biodegradable material is mainly produced by manufacturing a mold and using casting or centrifugation, and these methods are difficult to continuously process and have limitations in mass production.

Nevertheless, as fields using a microneedle is increasing, the need for development of a process for mass production continues to be raised.

DISCLOSURE

Technical Problem

A problem to be solved by the present disclosure is to provide a method for preparing microneedles and a microneedle patch through a continuous process and an apparatus used therein.

Technical Solution

One aspect of the present disclosure is to provide a conveyor apparatus for continuous production of microneedles comprising a microneedle mold of a porous material; a tray on which the mold is placed; and a conveyor belt to which the tray moves, and comprising an input unit along movement of the conveyor belt; an applying unit which supplies and applied a microneedle mixed solution to the mold; a filling unit which fills the mixed solution in the micro-space of the mold; a drying unit which dries the moisture of the mixed solution; and a separating unit which separates microneedle prepared in the drying unit from the mold, wherein an apparatus for forming decompression or vacuum to the bottom of the mold is equipped in the filling unit.

Conventionally, a method for produce a microneedle is a method for preparing a mold and producing a mixed solution to fill the mixed solution to the mold through casting or centrifugation and dry the moisture comprised in the mixed solution, but this is a batch or cell method that produces it by separating each process such as filling and drying, and the like, and therefore there are difficulties for mass production.

Accordingly, the present inventors, after a long study, have developed a method for using a conveyor belt-type continuous process, preparing a microneedle mole by a porous material, and forming a physical force by decompression or vacuum to the bottom of the mold, to allow a polymer solution to penetrate the micro-space of the mold, and thereby they have solved the aforementioned difficulties and have developed a method which can continuously produce microneedles and microneedle patches and an apparatus used therefor.

A suction or decompression apparatus forming decompression or vacuum is installed in the filling unit of the conveyor apparatus separately, and it refers to an apparatus forming a physical force only to the bottom, by forming decompression or vacuum, preferably, forming vacuum to the bottom of the mold.

There may be various modes for the method forming decompression or vacuum only to the bottom of the mold, and according to one embodiment, the bottom of the tray in which the mold of a porous material is arranged is penetrated, and the suction or decompression apparatus is equipped so as to be positioned at the bottom of the tray, and a physical force may be formed to the bottom.

According to another embodiment, the tray on which the mold of a porous material is arranged has a space where air can stay inside of the tray, and the tray has pathway(s) or hole(s) formed in the ceiling of the space through which air can pass, and the suction or decompression apparatus forms decompression or vacuum in the inner space of the tray, thereby forming a physical force to the bottom of the mold.

As the apparatus forming decompression or vacuum to the bottom of the mold, for example, there are a suction apparatus, a vacuum pump apparatus, a decompressor, an orifice pressure reducer for decompression, an elevated tank decompression apparatus, a decompression valve, and the like, but not limited thereto.

In the conveyor apparatus of the present disclosure, in the tray, one microneedle mold may be arranged, or a plurality of molds, for example, 1 to 20, 1 to 10 or 1 to 4 molds may be arranged.

The microneedle mold may have a number of fine engraved patterns, and it may be prepared by a porous polymer selected from the group consisting of PDMS (Poly dimethyl siloxane), PMHS (Polymethyl hydrosiloxane), porous silicon, porous polyurethane and porous PMMA (Polymethyl methacrylate).

In a preferable embodiment, the microneedle mold may be prepared by a porous silicon material comprising PDMS and PMHS.

The porous silicon material introduces a nanoporous pore into a silicon structure, and essential requirements for production of the porous silicon for use in the different application field may select appropriate production parameters to determine the form and shape of the pore. In the chemical and biological sensing application field, the surface area increasing the interest in porous silicon is large, and therefore there may be a large amount of bonds on the silicon surface, and the porous silicon may be prepared through constant current, gas, pulse iodine, chemical, orphotochemical etching procedures and/or strain etching.

In the porous material, a nanopore having a pore width of nanometer level may be formed, and for example, a macropore having a diameter of 50 nm or higher, a mesopore having a diameter of 2 to 50 nm and/or a micropore having a diameter of 2 nm or less, but not limited thereto.

Other aspect of the present disclosure is to provide a method for producing microneedles by a continuous process using a conveyor, comprising a) arranging a microneedle mold of a porous material on a tray; b) inputting the tray on a conveyor belt; c) supplying and applying a microneedle mixed solution in the mold; d) forming decompression or vacuum to the bottom of the mold to fill the mixed solution in a micro-space of the mold; e) drying the moisture of the mixed solution to produce microneedles; and f) separating the produced microneedles from the mold.

As a material composing the microneedle mixed solution according to the present disclosure, general synthetic and natural polymers, preferably, water-soluble polymers may be used, or self-dissolving or biocompatible materials may be used.

In one embodiment, the microneedle mixed solution may comprise any one or more selected from the group consisting of biocompatible polymers including poly(lactide), poly (glycolide), poly(lactide-co-glycolide), polyanhydride, polyorthoester, polyetherester, polycaprolactone, polyesteramide, poly(butyric acid), poly(valeric acid)), polyurethane or copolymer thereof; and polyacrylate, ethylene-vinylacetate polymer, acrylic substituted cellulose acetate, non-degradable polyurethane, polystyrene, polyvinyl chloride, polyvinyl fluoride, poly(vinyl imidazole), chlorosulfonate polyolefins, polyethylene oxide or copolymer thereof.

Preferably, the microneedle mixed solution is a material which is dissolved and absorbed in the body when inserted into skin, and for example, hyaluronic acid, sodium carboxymethyl cellulose, vinylpyrrolidone-vinylacetate copolymer, polyvinyl alcohol, polyvinyl pyrrolidone, saccharide or mixture thereof may be used, and as the saccharide, xylose, sucrose, maltose, lactose, trehalose or mixture thereof may be used.

More preferably, the microneedle mixed solution may comprise hyaluronic acid, sodium carboxymethyl cellulose and saccharide, and most preferably, it may comprise sodium carboxymethyl cellulose of 1 to 60% by weight, hyaluronic acid of 1 to 60% by weight, and saccharide of 3 to 60% by weight, based on the total weight of the composition for producing a microneedle, and it is much more preferable that the saccharide is trehalose.

The microneedle mixed solution according to the present disclosure may further comprise a solubilizing agent, a plasticizer, a surfactant, a preservative, an anti-inflammatory agent and the like, in addition to the aforementioned base compounds. As the plasticizer, for example, polyols such as ethylene glycol, propylene glycol, dipropylene glycol, butylene glycol, glycerin, and the like, may be used alone or in combination. In particular, as the result of various evaluations, glycerin is more preferable. As this plasticizer, various components known in the art may be suitably selected and used.

The microneedle mixed solution according to the present disclosure may further comprise additional components for causing additive or synergistic actions depending on a target material.

In the microneedle mixed solution according to the present disclosure may comprise various target materials selectively, and the target material may be for example, a drug, a vaccine, a nutrient or a component for cosmetics, depending on the use, but not limited thereto, and it may comprise a cell, a protein, a nucleic acid, a peptide, a polysaccharide, a lipid and the like. The target material may be present between materials (base compounds) forming the microneedle mixed solution in a form impregnated in the microneedle mixed solution, or may be present in a form that the materials (base compounds) forming the microneedle mixed solution surround the target material, but not limited thereto.

On the other hand, the method of the present disclosure may further comprise adhering a support comprising an adhesive to the produced microneedles between the steps e) and f), and in this case, prepared microneedles may be easily separated from the mold using the support comprising an adhesive.

The support comprising an adhesive may have adhesion on the surface contacting skin, and herein "adhesion" means a sticky property, and the degree of sticking is not particularly limited, and it is understood that it has adhesion when it does not fall off, when the patch touches a certain contact surface such as skin and the like.

The adhesive support (patch) may use a flexible material in consideration of the curve of skin, and the like, and for example, an acrylic or rubber-based adhesive having adhesion may be applied on the sheet having a material of for example, polyurethane, polyethylene, polyester, polypropylene, polyvinyl chloride, and the like. The adhesive may be applied for example, in a thickness of 1 to 100 μm.

In one example, in the patch, a hydrocolloid adhesive may be used. The hydrocolloid adhesive may be a form in which hydrophilic hydrocolloid particles are dispersed in a hydrophobic polymer matrix by mixing a tackifier to a hydrophilic polymer and a hydrophobic polymer. The tackifier may include for example, rosin ester, and the like, and all tackifiers commonly used for the hydrocolloid adhesive in the art may be included.

In other example, the hydrocolloid adhesive may be adhered to the microneedle in a laminated form on the film of polyurethane, polyethylene, polypropylene, polyvinyl chloride or polyester.

The form of the adhesive support is not particularly limited, and the form may be prepared in consideration of possibility of contact with skin, shape of the microneedle array, and the like.

The adhesive support may comprise numerous micro-sized holes, and may have a structure in which moisture (or liquid) can be transferred to the microneedle along the holes. The number of the holes is not limited, and it may be appropriately selected in consideration of the difference in solubility according to the materials of the microneedle, and the like.

In addition, the adhesive support may comprise a drug or cosmetic component-containing matrix or reservoir. As such, when the skin adhesive support or patch contains a medically, pharmaceutically or cosmetically active component, there is an advantage that the active component can quickly move into skin from the patch.

The medically, pharmaceutically or cosmetically active component may be a medicinal material such as a chemical compound having a small molecular weight, a protein, an antibody, and the like, or a beauty material such as a vaccine, Botox, retinol, tocopherol, vitamin C, and the like.

Effects

By using the microneedle production method and apparatus according to the present disclosure, continuous mass production of microneedles is available, and therefore it is possible to reduce the input of manpower and produce a large amount of products compared to the conventional production method.

BRIEF DESCRIPTION OF THE DRAWINGS

FIG. 1 shows a schematic plan view of a tray on which a mold is placed.

FIG. 2 illustrates the schematic order or process of production of microneedles according to one embodiment of the present disclosure.

FIG. 3 illustrates the continuous production process or apparatus of microneedles according to one embodiment of the present disclosure.

MODE FOR INVENTION

Hereinafter, the present disclosure will be described in detail by examples and the like to help understanding of the present disclosure. However, the examples according to the present disclosure may be modified into other various forms, and the scope of the present disclosure should not be construed to be limited by the following examples. The examples of the present disclosure are provided to more completely describe the present disclosure to those skilled in the art.

Herein, a singular expression includes a plural expression unless the context clearly indicates otherwise. Herein, terms such as "comprise" or "have" or the like should be understood that they are intended to indicate that a feature, step, operation, component, part or combination thereof described in the specification exists, and they do not exclude the possibility of presence or absence of one or more other features, steps, operations, components, parts or combinations thereof in advance.

Unless defined otherwise, all terms used herein including technical or scientific terms, have the same meaning as commonly understood by those skilled in the art to which the present disclosure pertains. Terms such as those defined in a commonly used dictionary should be interpreted as having meanings consistent with meanings in the context of related technologies, and should not be construed in an ideal or excessively formal sense, unless explicitly defined in the present application.

In the present example, 4 porous microneedle molds made of a PDMS (PolyDiMethylSiloxane) material were fixed on a tray with a passage in which air could pass as shown in FIG. 1, and the tray in which molds were fixed is inputted on a conveyor belt.

A microneedle mixed solution was prepared by dissolving sodium carboxymethyl cellulose of 40 parts by weight, hyaluronic acid of 40 parts by weight and trehalose of 20 parts by weight in purified water, and then adding Glycerin, HCO-40 and Peptide solution (Peptide 10%, DPG 90%), and a resin fluid in which it was dissolved was supplied to a hopper of the conveyor apparatus.

When the tray in which porous molds were fixed reached an applying unit according to movement of the conveyor belt, the microneedle mixed solution was supplied and applied inside the molds using the hopper.

Then, by a suction device which was installed on the bottom and operated when the tray reached the filling unit according to movement of the conveyor belt, the bottom of the mold was vacuum sucked, and thereby, the mixed solution was deeply filled in a needle forming unit of the mold. Then, after drying it at 70° C. for 3 hours, microneedles were separated from the porous silicone mold using an adhesive film.

The microneedle patch produced in this way may be stored and delivered in a package.

On the other hand, FIG. 3 illustrates the continuous production process or apparatus of microneedles, and 1, 2, 3, 4, 5 of FIG. 3 mean the tray in which molds are arranged, and it moves according to movement of the conveyor belt. Each process proceeds in the order listed, and it consists of an inputting unit, an applying unit, a filling unit, a drying unit and a separating unit. The filling unit forms vacuum inside the tray, and through this, the mixed solution is filled in a micro-space of porous molds.

Although described above with reference to preferable examples of the present disclosure, those skilled in the art can understand that the present disclosure can be variously modified and changed within a range without departing from the spirit and scope of the present disclosure described in the following claims.

The invention claimed is:

1. A conveyor apparatus for continuous production of microneedles comprising:
   a microneedle mold of a porous material;
   a tray on which the mold is placed;
   a conveyor belt on which the tray moves;
   an applying unit which supplies and applies a microneedle mixed solution to the mold,
   wherein the applying unit includes a hopper;
   a filling unit which fills the mixed solution in the in a micro-space of the mold; and
   a drying unit having a dryer which dries moisture of the mixed solution,
   wherein the filling unit has an apparatus for forming decompression or vacuum to a bottom of the mold, and
   wherein the production of microneedles takes place continuously on the conveyor belt.

2. The conveyor apparatus according to claim 1, wherein a bottom of the tray has pathway(s) or hole(s) through which air can pass, and wherein the apparatus forming decompression or vacuum is equipped under the tray.

3. The conveyor apparatus according to claim 2, wherein the apparatus forming decompression or vacuum is a suction apparatus.

4. The conveyor apparatus according to claim 2, wherein the microneedle mold has a fine engraved pattern.

5. The conveyor apparatus according to claim 2, wherein the porous material is a porous polymer selected from the group consisting of Poly dimethyl siloxane (PDMS), Polymethyl hydrosiloxane (PMHS), porous silicon, porous polyurethane and porous Polymethyl methacrylate (PMMA).

6. The conveyor apparatus according to claim 2, wherein a plurality of molds are arranged on the tray.

7. The conveyor apparatus according to claim 1,
wherein the tray has a space inside thereof containing air, and has pathway(s) or hole(s) in a ceiling of the space through which air can pass, and
wherein the apparatus forming decompression or vacuum is equipped so that decompression or vacuum is formed inside of the tray.

8. The conveyor apparatus according to claim 7, wherein the apparatus forming decompression or vacuum is a suction apparatus.

9. The conveyor apparatus according to claim 7, wherein the microneedle mold has a fine engraved pattern.

10. The conveyor apparatus according to claim 7, wherein the porous material is a porous polymer selected from the group consisting of Poly dimethyl siloxane (PDMS), Polymethyl hydrosiloxane (PMHS), porous silicon, porous polyurethane and porous Polymethyl methacrylate (PMMA).

11. The conveyor apparatus according to claim 7, wherein a plurality of molds are arranged on the tray.

12. The conveyor apparatus according to claim 1, wherein the apparatus forming decompression or vacuum is a suction apparatus.

13. The conveyor apparatus according to claim 1, wherein the microneedle mold has a fine engraved pattern.

14. The conveyor apparatus according to claim 1, wherein the porous material is a porous polymer selected from the group consisting of Poly dimethyl siloxane (PDMS), Polymethyl hydrosiloxane (PMHS), porous silicon, porous polyurethane and porous Polymethyl methacrylate (PMMA).

15. The conveyor apparatus according to claim 1, wherein a plurality of molds are arranged on the tray.

16. A method for producing microneedles by a continuous process using a conveyor, comprising
a) arranging a microneedle mold of a porous material on a tray;
b) putting the tray on a conveyor belt;
c) supplying and applying a microneedle mixed solution in the mold;
d) forming decompression or vacuum to a bottom of the mold to fill the mixed solution in a micro-space of the mold;
e) drying moisture of the mixed solution to produce microneedles; and
f) separating the produced microneedles from the mold,
wherein the steps of b) to d) take place continuously on the conveyor belt.

17. The method according to claim 16, further comprising adhering a support comprising an adhesive to the produced microneedles between the steps e) and f).

18. The method according to claim 17, wherein the support is a skin adhesive patch.

* * * * *